(12) United States Patent
Hatano et al.

(10) Patent No.: US 8,586,025 B2
(45) Date of Patent: Nov. 19, 2013

(54) METHOD OF INHIBITING METHANOGENESIS

(75) Inventors: Isami Hatano, Tokyo (JP); Makoto Shoda, Tokyo (JP); Yoichi Ishikawa, Tokyo (JP)

(73) Assignees: Able Corporation, Tokyo (JP); Isami Hatano, Tokyo (JP)

( * ) Notice: Subject to any disclaimer, the term of this patent is extended or adjusted under 35 U.S.C. 154(b) by 0 days.

(21) Appl. No.: 13/696,405

(22) PCT Filed: May 13, 2011

(86) PCT No.: PCT/JP2011/061038
§ 371 (c)(1),
(2), (4) Date: Jan. 30, 2013

(87) PCT Pub. No.: WO2011/145516
PCT Pub. Date: Nov. 24, 2011

(65) Prior Publication Data
US 2013/0129684 A1  May 23, 2013

(30) Foreign Application Priority Data

May 18, 2010 (JP) ................................. 2010-114271

(51) Int. Cl.
*A61K 39/02* (2006.01)
*A23K 1/18* (2006.01)
*A23K 1/16* (2006.01)

(52) U.S. Cl.
USPC ........................... 424/93.4; 424/442; 426/623

(58) Field of Classification Search
USPC .................................. 424/93.4, 442; 426/623
See application file for complete search history.

(56) References Cited

FOREIGN PATENT DOCUMENTS

| JP | H07-322828 | 12/1995 | ............... A23K 1/16 |
| JP | H09-104606 | 4/1997 | ............. A01N 63/00 |
| JP | 2002-199875 | 7/2002 | ............... C12N 1/20 |
| JP | 2009-201354 | 9/2009 | ............... C12N 1/00 |

OTHER PUBLICATIONS

Bergey's Manual of Determinative Bacteriology (Eighth Edition 1974, R.E. Buchanan and N.E. Gibbons, co-editors, pp. 274-275, especially p. 274, second column).*
Anderson, et al., (1998) "Use of a novel nitrotoxin-metabolizing bacterium to reduce ruminal methane production." *Bioresour Technol.*, vol. 64:89-95.
Asanuma, et al., (2003) "Isolation of new nitrite-reducing bacteria, and augmentation of nitrite reduction in the rumen by introducing one of the isolated bacteria." *Bulletin of the Faculty of Agriculture*, Meiji University, No. 137:1-17, Abstract only.
Mphande, et al., (1995) "Methane emission and methanogen status of Indian rice soil." *Bioresour Technol.*, vol. 54:155-158.
Yang, et al., (1998) "Effect of environmental conditions on methane production and emission from paddy soil." *Agriculture, Ecosystems and Environment*, vol. 69:69-80.
International Search Report (ISR) in PCT/JP2011/061038, dated Aug. 16, 2011.

* cited by examiner

*Primary Examiner* — Jon P Weber
*Assistant Examiner* — Larry Moore
(74) *Attorney, Agent, or Firm* — Harness, Dickey & Pierce, P.L.C.; J. Timothy Keane; Kisuk Lee

(57) ABSTRACT

The object of the present invention is to provide a technique to inhibit methanogens from producing methane. The use of *Alcaligenes faecalis* can inhibit methanogens from producing methane.

5 Claims, 1 Drawing Sheet

METHOD OF INHIBITING METHANOGENESIS

CROSS-REFERENCE TO RELATED APPLICATIONS

This application is a National Phase Application of PCT Application No. PCT/JP2011/061038 filed on May 13, 2011, which claims the benefit and priority to Japanese Patent Application No. 2010-114271 filed May 18, 2010. The entire disclosures of the applications identified in this paragraph are incorporated herein by references.

FIELD

The present invention relates to a technique to inhibit methanogens from producing methane.

BACKGROUND

In recent years, the issue of global warming has been attracting attention amid growing interest in environmental problems. Global warming develops as greenhouse gas concentrations are raised in the atmosphere. Greenhouse gases such as carbon dioxide, methane, and perfluorocarbons (PFCs) have strong absorption in the infrared region, and when they are released into the air, they absorb the energy radiated from the Earth's surface and give off a part of the energy to the underlying Earth's surface. Namely, a part of the energy given off from the Earth's surface is returned to the Earth's surface by greenhouse gases, and the so-called greenhouse effect causes global warming.

In the 3rd Conference of the Parties to the UNFCCC, which was held in 1997, the greenhouse gas reduction targets were set for developed countries, and it was decided to reduce certain levels of greenhouse gases between the years 2008 and 2012, on the basis of the levels in 1990. The assessment of the greenhouse effect of greenhouse gases based on the volume of greenhouse gases and their global warming potentials shows that carbon dioxide is the biggest contributor to the greenhouse effect, followed by methane. Particularly, methane (global warming potential: 21) is higher in global warming potential than carbon dioxide (global warming potential: 1) and even a small amount of methane greatly affects global environment. Against these backgrounds, there is a strong demand for a technique to inhibit methane production.

In general, methane is produced through methane fermentation carried out by methanogenic bacteria (methanogens), and in the environment, methane is known to be produced chiefly from the ruminant stomach (rumen) and paddy fields. Methanogens synthesize methane under anaerobic conditions. In the ruminant stomach, organic acids are produced in the phase of the digestion of grass and the like and the organic acids are converted into methane by methanogens. In paddy fields, methanogens decompose organic substances such as rice stubble to produce methane. The methane derived from ruminants and paddy fields is reported to account for 20-30% of the total methane, and if the methanogenesis in these sources can be inhibited, methane, which is a greenhouse gas, can be reduced to a great degree.

The techniques to inhibit methanogenesis which have been reported so far are methods such as use of cysteine (Patent Document 1) and use of lactic acid bacteria and the like (Patent Document 2).

CITATION LIST

Patent Document

Patent Document 1: JP H07-322828 A
Patent Document 2: JP 2009-201354 A

SUMMARY

Technical Problem

The object of the present invention is to provide a technique to inhibit methanogens from producing methane.

Solution to Problem

In view of the circumstances as described above, the present inventors intensively have studied a technique to inhibit methanogens from producing methane and found that certain *Alcaligenes* bacteria can inhibit such methanogenesis effectively under anaerobic conditions. The present invention has been thus accomplished. More specifically, in the present invention, *Alcaligenes faecalis*, especially, *Alcaligenes faecalis* No. 4 (FERM BP-11247), is used to suppress methane fermentation to inhibit methanogenesis.

To date, *Alcaligenes faecalis*, which is used in the present invention, has been known to convert ammonia directly into nitrogen gas under aerobic conditions (JP 2002-199875 A). In addition, use of *Alcaligenes faecalis* as a plant disease control agent has been suggested (JP H09-104606 A). The properties of the *Alcaligenes faecalis* stated above under anaerobic conditions have not been known, but this time the present inventors have confirmed that the *Alcaligenes faecalis* also grows using (utilizing) acetic acid and ammonia ($NH_4^+$) under anaerobic conditions (see Test Example described later). The present inventors also have found that the application of the *Alcaligenes faecalis* to a methane fermentation system can inhibit methanogenesis.

Specifically, the present invention relates to, but is not limited to, a methanogenesis inhibitor comprising *Alcaligenes faecalis* capable of using acetic acid as a substrate. Particularly preferred *Alcaligenes faecalis* for use is *Alcaligenes faecalis* strain No. 4. The administration of the methanogenesis inhibitor of the present invention to ruminants can inhibit the production of methane emitted from the ruminants. In addition, the application of the methanogenesis inhibitor of the present invention to paddy fields, lakes, or aquaculture ponds can inhibit the production of methane emitted from the paddy fields, lakes, or aquaculture ponds. Further, when the methanogenesis inhibitor of the present invention is put in a methane fermentation tank, the inhibitor can inhibit methane from being produced in methane fermentation in the reaction tank.

The present invention also relates to a feed for ruminants comprising the methanogenesis inhibitor stated above and to a fertilizer comprising the inhibitor.

The present invention further relates to a method of inhibiting methanogenesis comprising applying *Alcaligenes faecalis* capable of using acetic acid as a substrate to a methane fermentation system.

Advantageous Effects

The present invention can inhibit methanogens from producing methane. In accordance with the present invention, the production of methane, which is one of greenhouse gases, can be inhibited and the invention thus contributes to the conservation of global environment.

DESCRIPTION OF EMBODIMENTS

Figure 1:
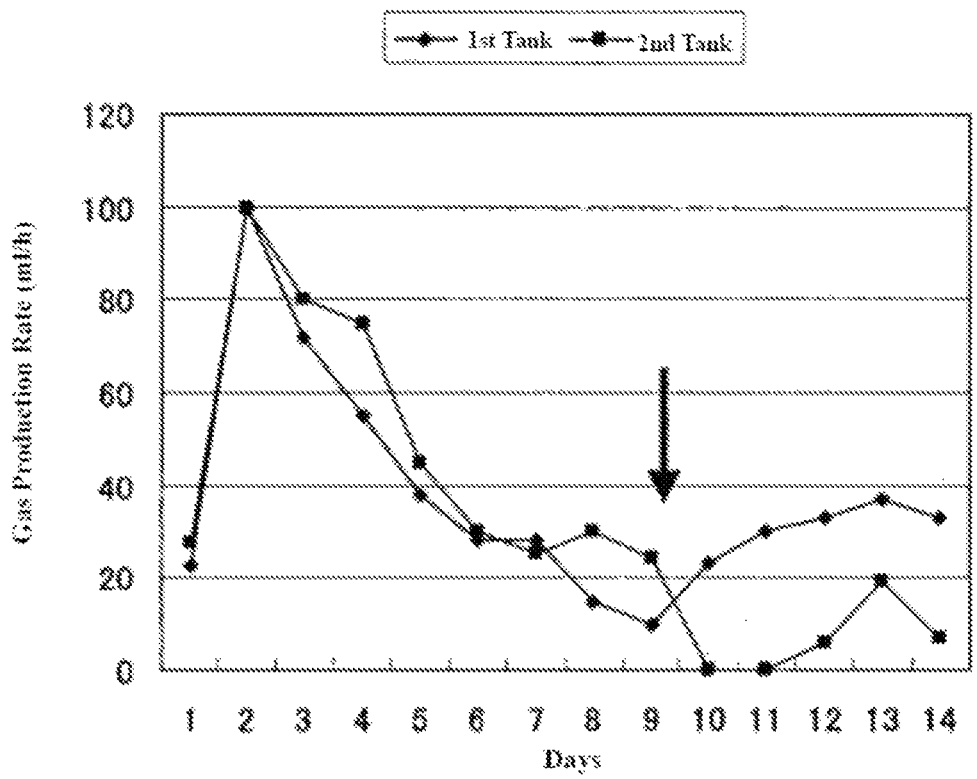
FIG. 1 is a graph showing that the *Alcaligenes faecalis* used in the present invention inhibited methanogens from producing methane. In the graph, the arrow indicates the timing of putting the *Alcaligenes faecalis* in a reaction tank.

In the present invention, *Alcaligenes faecalis*, especially, *Alcaligenes faecalis* No. 4 (FERM BP-11247), is used to inhibit methanogenesis. More specifically, in the present invention, *Alcaligenes faecalis*, especially, *Alcaligenes faecalis* No. 4, is used to suppress methane fermentation to inhibit methanogenesis.

From one point of view, the present invention is directed to a methanogenesis inhibitor comprising *Alcaligenes faecalis*. From another point of view, the present invention is directed to a method of inhibiting methanogenesis comprising applying *Alcaligenes faecalis* to a methane fermentation system.

It is to be noted that "inhibiting" methanogenesis in the present invention includes "preventing" methanogenesis, which means that no methane is substantially produced.

*Alcaligenes faecalis* One example of the microorganisms used in the present invention is a microorganism separated from the soil in Kanagawa Prefecture and it belongs to *Alcaligenes faecalis* and has the bacteriological properties shown below. This microorganism has been deposited with the International Patent Organism Depositary, National Institute of Advanced Industrial Science and Technology (at Tsukuba Central 6, 1-1-1 Higashi, Tsukuba, Ibaraki, Japan), as *Alcaligenes faecalis* No. 4 as of Apr. 9, 2010, and the accession number is FERM BP-11247.

TABLE 1

Bacteriological properties of *Alcaligenes faecalis* strain No. 4

| Shape | Rod | Utilization properties: | |
|---|---|---|---|
| Gram stainability | − | Glucose | − |
| Presence or absence of spores | − | L-arabinose | − |
| Motility | + | D-mannose | − |
| Oxidase | + | D-mannitol | − |
| Catalase | + | N-acetyl-D-glucosamine | − |
| OF test | − | Maltose | − |
| Reduction of nitrate | − | Potassium gluconate | − |
| Indole production | − | N-capric acid | + |
| Glucose fermentability | − | Adipic acid | − |
| Arginine dihydrolase | − | DL-malic acid | + |
| Urea decomposition | − | Sodium citrate | + |
| Esculin decomposition | − | Phenyl acetate | + |
| Gelatin liquefaction | − | | |
| PNPG* decomposition | − | | |

*p-nitrophenyl β-D-glucoside

The *Alcaligenes faecalis* used in the present invention is preferably *Alcaligenes faecalis* No. 4, which is stated above, but is not limited thereto. All the microorganisms belonging to *Alcaligenes faecalis* can be used as long as they can use acetic acid as a substrate under anaerobic conditions and have the capability of inhibiting methanogenesis (the property of suppressing methane fermentation). Incidentally, the microorganism used in the present invention may be selected in accordance with, for example, the methods described in Test Example and Example, which are shown later. In addition, *Alcaligenes faecalis* strain No 4 stated above, which has the property of suppressing methane fermentation, can be used as an original strain to obtain its genetic mutants used as *Alcaligenes faecalis* in the present invention by improving the above property through natural or induced mutation. These mutants can be prepared by known methods; for example, the mutants can be selected after an artificial mutation treatment of the original strain with ultraviolet irradiation or a drug such as N-methyl-N'-nitro-N-nitrosoguanidine (NTG).

The cell mass of the *Alcaligenes faecalis* used in the present invention can be obtained by culture (bacterial growth culture) under common culture conditions. Any culture medium may be used as long as it allows the growth of the *Alcaligenes faecalis* in the present invention, but the *Alcaligenes faecalis* is preferably cultured in a medium supplemented with ammonium salt as a nitrogen source. The *Alcaligenes faecalis* also can grow either in an organic medium composed primarily of peptone, yeast extract, and the like or in an inorganic medium composed primarily of potassium phosphate, magnesium sulfate, and the like. The organic medium is, for example, a L medium containing 10 g/L of peptone, 5 g/L of yeast extract, and 5 g/L of sodium chloride, and the inorganic medium is, for example, a MM medium containing 14 g/L of $K_2HPO_4$, 6 g/L of $KH_2PO_4$, 2 g/L of $(NH_4)_2SO_4$, 15 g/L of trisodium citrate dihydrate, and 0.2 g/L of $MgSO_4 \cdot 7H_2O$. The culture can be performed under either anaerobic or aerobic conditions, but aerobic conditions are preferred in growing a microorganism. Any culture method can be used, and for example, aerated and agitated culture, shaking culture, or solid culture can be applied, and an aerated and agitated liquid culture enables the culture of a great amount of the bacterium for a short period of time. The culture conditions are not particularly limited, but the culture temperature is preferably 20-40° C., more preferably 25-30° C. The culture pH is preferably 6.0-8.0, more appropriately about 7. The appropriate culture period is within the range of 15-72 hours. Either batch culture or continuous culture can be selected.

In the present invention, *Alcaligenes faecalis* in culture can be used directly without being separated from the culture. Alternatively, the culture can be used either in dried form or can be combined with various additives and used as a formulation such as a wettable powder. The *Alcaligenes faecalis* in the present invention which is fixed to a carrier also can be used; for example, the present invention also can be carried out by fixing the bacterium to a carrier and flowing an object to be treated across the surface of the carrier under anaerobic conditions.

The details of the reason why *Alcaligenes faecalis* inhibits methanogens from producing methane in the present invention remain unclear and the present invention is not bound thereby. Our speculation is, however, as follows: methanogens use an organic acid (e.g., acetic acid) as a substrate for methane fermentation, while the *Alcaligenes faecalis* used in the present invention grows using acetic acid and ammonia ($NH_4^+$) as a substrate under anaerobic conditions, as described above; thus, the organic acid to be used by methanogens is consumed by the *Alcaligenes faecalis* in the present invention, and as a result, methane fermentation is suppressed.

Methane Fermentation System The methane fermentation system in the present invention is a system in which methane is produced by methanogens under anaerobic conditions. The methane fermentation system thus includes, for example, waste treatment in an anaerobic reaction tank using activated sludge or the like, methane fermentation in the rumen of ruminants, and methane fermentation in paddy fields and the like. It should be noted that in the present invention, "the methane fermentation system" also includes a system in which methane fermentation is not in progress at present but will occur in the future; for example, in the present invention, *Alcaligenes faecalis* can be applied to paddy fields and the like in advance, thereby preventing future methanogenesis.

Methanogens (methane bacteria) are microorganisms which synthesize methane under anaerobic conditions. They are present widely in the digestive organs of animals, marsh, submarine sediment, and the Earth's crust and synthesize most of methane released on the Earth. All the species of methanogens are classified under the phylum *Euryarchaeota* (Archaea). Some methanogens coexist with other bacteria or grow in competition among substrates, and for example, there are some cases where methanogens coexist with Eubacteria which decompose lower fatty acids to produce acetic acid. Further, in recent years, the application of methanogens to sludge treatment or water purification, and the like have been attempted.

In general, methanogens use organic acids and carbon dioxide as carbon sources to produce methane. For example, methane bacteria belonging to the class *Methanosarcinacea* use carbon monoxide, acetic acid, methanol, methyl thiol, methyl amine, and the like to produce methane. The substrates used by methanogens vary depending on their growing environment. For example, most of the freshwater sediment in lakes, etc. is degraded to carbon dioxide, formic acid, or acetic acid. Thus, the volume of acetic acid is large in freshwater and about 60% of methane produced in freshwater is deemed to be produced from acetic acid.

In the above-mentioned methane fermentation system in the present invention, methanogens may be separated ones or may be ones which live in organic wastes and the like (mixed microorganisms, microbial flora). Methanogens which live in organic wastes, activated sludge, and the like include, for example, the microorganisms belonging to the genus *Methanococcus, Methanobacterium*, or *Methanosarcina*, but are not limited thereto.

In the present invention, the temperature for methane fermentation is preferably 20-40° C. The pH for methane fermentation is preferably 6.0-8.0, more appropriately about 7. If the methane fermentation is carried out in a reaction tank, either batch methane fermentation or continuous methane fermentation may be selected.

If the *Alcaligenes faecalis* used in the present invention is intended to be used to inhibit methanogenesis in a methane fermentation system using activated sludge or the like, this bacterium may be put in an anaerobic reaction tank or may be supported on a porous carrier or the like when put in a reaction tank.

Inhibition of Methane Production from Ruminants

The administration of the *Alcaligenes faecalis* in the present invention to ruminants can inhibit the production of methane emitted from them. Thus, the present invention is directed to a method of inhibiting the production of methane emitted from ruminants, which comprises the administration of *Alcaligenes faecalis* to ruminants. From another point of view, the present invention is directed to a methanogenesis inhibitor for administration to ruminants. From still another point of view, the present invention is directed to a feed for ruminants comprising *Alcaligenes faecalis*.

Ruminants generally have a plurality of stomachs, and in their rumens, methane is produced by methanogens under anaerobic conditions. It is deemed that particularly in the stomach of ruminants, organic acids are produced in the phase of the digestion of food such as grass and are then converted into methane by methanogens. The volume of methane produced by fermentation in the digestive organs of domestic or wild ruminants is estimated to be equivalent to about 16% of the total methane released on the Earth. Hence, if the inhibition of methanogenesis in ruminants is possible, it is very useful. The inhibition of methanogenesis in ruminants also inhibits the carbon sources and the like in feed from being consumed by methane fermentation, and as a result, the feed efficiency (conversion ratio) is improved.

In the present invention, a ruminant is an animal having the reticulorumen and has a plurality of stomachs in the digestive system. The ruminant includes, for example, cow, goat, sheep, and buffalo and includes not only domestic ruminants but also wild ruminants. Since the pH of the rumen of ruminants is not so acidic, the *Alcaligenes faecalis* in the present invention can have the property of suppressing methane fermentation in the rumen of ruminants.

In the digestive organs of ruminants, methanogens use an organic acid such as acetic acid for methane fermentation to produce methane. When the *Alcaligenes faecalis* in the present invention is administered to ruminants, the organic acid such as acetic acid is consumed, which can suppress or inhibit methanogenesis carried out by methanogens and thus inhibit the production of methane emitted from ruminants. Hence, in accordance with the present invention, the production of methane contained in the burps (eructations) of ruminants can be inhibited, which is very advantageous in that the inhibition reduces not only global warming gases but also odor. It is to be noted that methane in the breath or in the rumen can be measured, for example, with a volatile hydrocarbon analyzer "Model TVA-1000B" (Mitsuwa Frontech Corp.)

The methanogenesis inhibitor of the present invention can be prepared through the culture of a microorganism, provided that no contamination with pathogenic bacteria is preferably confirmed. If the inhibitor is to be formulated, it may be mixed with a carrier, and if needed, it also may be mixed with dispersant, stabilizer, diluent, binder, and the like. The dosage form can be an intended one such as granule, powder, or powdered drug.

Further, if the inhibitor is to be formulated, a culture substrate such as rice bran, wheat bran, soybean meal, soy germ, soy sauce cake, potato pulp, konjac fine powder (Tobiko), palm oil residue, calcium-containing materials, or starches can be contained. Examples of the calcium-containing materials include egg shell, oyster shell, calcium carbonate, calcium lactate, calcium phosphate, calcium propionate, or mixtures of two or more of these calcium-containing materials. Examples of the starches include corn, sorghum, other feed grains, sweet potato starch, potato starch, corn starch, wheat starch, tapioca and sago starch, various modified starches, glucose, isomerized sugar, starch syrup, and the like.

The dosage amount of the inventive methanogenesis inhibitor to ruminants is not particularly limited as long as the inhibitor produces an inhibitory effect on methanogenesis, and the dosage amount can be determined as appropriate according to the types of the ruminants, their growing stages, rearing environment such as season and location, and the like.

The inventive methanogenesis inhibitor may be used alone or in combination with a feed. If the methanogenesis inhibitor is administered separately from a feed, the inhibitor may be administered at any time as long as the feed remains in the rumen. It is preferred that the methanogenesis inhibitor is present in the rumen before methane is produced and that the methanogenesis inhibitor is administered immediately before or at the same time as feeding.

Inhibition of Methane Production from Paddy Fields and Elsewhere

The *Alcaligenes faecalis* used in the present invention can be applied to paddy fields, lakes, or aquaculture ponds to inhibit the production of methane emitted from them. Thus, the present invention is directed to a method of inhibiting the production of methane emitted from paddy fields and elsewhere, which comprises applying *Alcaligenes faecalis* to paddy fields and elsewhere. From another point of view, the present invention is directed to a methanogenesis inhibitor for application to paddy fields and elsewhere. From still another point of view, the present invention is directed to a fertilizer comprising the methanogenesis inhibitor.

In general, organic substances exist such as corroded rice stubble and other corroded animals and plants, animal wastes, and other wastes, at the bottom of paddy fields and lakes, which are environment where methane is likely to be produced through methane fermentation by methanogens. Methane produced from paddy fields and elsewhere is a main source of methane release on the Earth, along with methane emitted from ruminants. Hence, if the inhibition of methanogenesis in paddy fields and elsewhere is possible, it is very useful.

In the present invention, *Alcaligenes faecalis* is applied to the locations where methane fermentation is carried out by methanogens, such as paddy fields, lakes, or aquaculture ponds. The application of *Alcaligenes faecalis* to paddy fields and elsewhere by means such as spraying can suppress methanogenesis carried out by methanogens and inhibit the production of methane emitted from paddy fields and elsewhere without use of chemical products. *Alcaligenes faecalis* No. 4, which is used in the present invention, has the inhibitory activity on the growth of various plant pathogens, as disclosed in JP H9-104606 A, and thus, spraying *Alcaligenes faecalis* No. 4 over farm lands such as paddy fields is advantageous.

The *Alcaligenes faecalis* used in the present invention can be prepared through its culture, provided that no contamination with pathogenic bacteria is preferably confirmed. If the *Alcaligenes faecalis* is to be formulated, it may be mixed with a carrier, and if needed, it also may be mixed with dispersant, stabilizer, diluent, binder, and the like. The dosage form can be an intended one such as granule, powder, or powdered drug.

Further, if the *Alcaligenes faecalis* is to be formulated, a culture substrate such as rice bran, wheat bran, soybean meal, soy germ, soy sauce cake, potato pulp, konjac fine powder (Tobiko), palm oil residue, calcium-containing materials, or starches can be contained. Examples of the calcium-containing materials include egg shell, oyster shell, calcium carbonate, calcium lactate, calcium phosphate, calcium propionate, or mixtures of two or more of these calcium-containing materials. Examples of the starches include corn, sorghum, other feed grains, sweet potato starch, potato starch, corn starch, wheat starch, tapioca and sago starch, various modified starches, glucose, isomerized sugar, starch syrup, and the like.

The shape, applied amount, and applied frequency of the inventive methanogenesis inhibitor are not particularly limited as long as the inhibitor produces an inhibitory effect on methanogenesis, and they can be determined as appropriate according to the environment to which the inhibitor is applied such as paddy fields, season, the production status of methane, and the like. The inventive methanogenesis inhibitor may be used alone or in combination with a fertilizer or the like. Moreover, for example, the culture of the *Alcaligenes faecalis* in the present invention or *Alcaligenes faecalis* separated therefrom can be suspended in water and then can be sprayed over paddy fields and elsewhere.

The present invention will be described more specifically showing Examples below, but is not limited thereto. It should be noted that parts, %, and the like as used herein are by weight, unless otherwise stated, and that each of the numerical ranges includes both endpoints.

EXAMPLES

Example

In two stirred reaction tanks each with a 1L capacity, a first tank (control) and a second tank (test), 800 ml each of sludge was put which was obtained by methane fermentation of food residues (organic industrial wastes such as onion and potato from food factories) (the sludge was obtained by fermentation at 37-38° C. for a retention time of 30 days). After that, methane fermentation was carried out for 14 days under the conditions of an initial pH of 7 at 33° C., while the sludge was being stirred gently. During the experiment, the head spaces of the reaction tanks were purged with nitrogen gas in order to maintain the anaerobic conditions.

At the start of the methane fermentation and every day after that, 800 ml of the nutrient sources as shown in Table 2 was added in solid state for the methane fermentation. Sodium acetate was used as a carbon source in the methane fermentation system in this example, and the monitoring of whether carbon was consumed was achieved by checking the pH of the system.

TABLE 2

| Amount of added nutrient sources (g/l) | |
|---|---|
| Sodium acetate | 10 |
| $KH_2PO_4$ | 0.3 |
| $NH_4Cl$ | 1 |
| $MgSO_4 \cdot 7H_2O$ | 0.1 |
| $CaCl_2 \cdot 2H_2O$ | 0.1 |
| Yeast extract | 0.1 |
| $CoCl_2 \cdot 2H_2O$ | 0.02 |

On the 9$^{th}$ day after the nutrient sources were added and the methane fermentation was started, 20 ml of a culture solution of *Alcaligenes faecalis* No. 4 (FERM BP-11247) (bacterial concentration: about $5 \times 10^8$ cells/ml) was added to the second tank (test) at 6 p.m. (see the arrow in FIG. 1).

Incidentally, the culture solution of *Alcaligenes faecalis* No. 4 was obtained as follows: after a liquid medium (see Table 3 for the composition) was aliquoted in 100 ml into shake flask with a 500 ml capacity, *Alcaligenes faecalis* No. 4 was inoculated into the prepared liquid medium and shaking culture was carried out at 30° C. for 72 hours.

TABLE 3

| Composition of liquid medium Composition of liquid medium (g/l, trace element solution is excluded) | |
|---|---|
| Sodium acetate | 14.6 |
| $K_2HPO_4$ | 14 |
| $KH_2PO_4$ | 6 |
| $(NH_4)_2SO_4$ | 2 |
| $MgSO_4 \cdot 7H_2O$ | 0.2 |
| Trace element solution | 2 ml/l |

(Note)
Trace element solution (g/l): EDTA·2Na: 57.1, $ZnSO_4 \cdot 7H_2O$: 3.9, $CaCl_2 \cdot 2H_2O$: 7.0, $MnCl_2 \cdot 4H_2O$: 5.1, $FeSO_4 \cdot 7H_2O$: 5.0, $(NH_4)_6Mo_7O_{24} \cdot 4H_2O$: 1.1, $CuSO_4 \cdot 5H_2O$: 1.6, $CoCl_2 \cdot 6H_2O$: 1.6

The volumes of the gas produced from the respective reaction tanks after the start of the methane fermentation were measured with graduated cylinders at 10 a.m. each day. The volumes of gas production per hour (ml/h) at the time of the measurements are shown in FIG. 1 and Table 4.

TABLE 4

| | Gas production rate | |
|---|---|---|
| Time period (days) | Gas production rate at 1st tank (control) (ml/h) | Gas production rate at 2nd tank (test) (ml/h) |
| 1 | 22.5 | 27.5 |
| 2 | 100 | 100 |
| 3 | 72 | 80 |
| 4 | 55 | 75 |
| 5 | 38 | 45 |
| 6 | 28 | 30 |
| 7 | 28 | 25 |
| 8 | 15 | 30 |
| 9 | 10 | 24 |
| 10 | 23 | 0 |
| 11 | 30 | 0 |
| 12 | 33 | 6 |
| 13 | 37 | 19 |
| 14 | 33 | 7 |

As seen from FIG. 1, the volume of gas production in the second tank had decreased considerably since *Alcaligenes faecalis* No. 4 was put in the tank. In addition, the gas chromatographic analysis result of the gas stated above confirms that methane accounted for 91-97% (V/V). It is clear from the above that the *Alcaligenes faecalis* used in the present invention markedly inhibited methanogenesis in the methane fermentation system.

Test Example

It was examined whether the *Alcaligenes faecalis* used in the present invention would grow using (utilizing) acetic acid and ammonia under anaerobic conditions.

A liquid medium (0.1 g/l of a yeast extract was added to the composition shown in Table 3) was aliquoted in 100 ml into flask with a 500 ml capacity. *Alcaligenes faecalis* No. 4 (FERM BP-11247) was inoculated into the prepared liquid medium and standing culture was carried out at 30° C. for 15 days. Incidentally, the gas phase portion of the flask was purged continuously with nitrogen gas.

During this culture period, the bacterial concentration (OD value), acetic acid concentration (g/l and ammonium ion ($NH_4^+$) concentration (g/l) of the culture solution were measured. The results are shown in FIG. 2.

Figure 2:
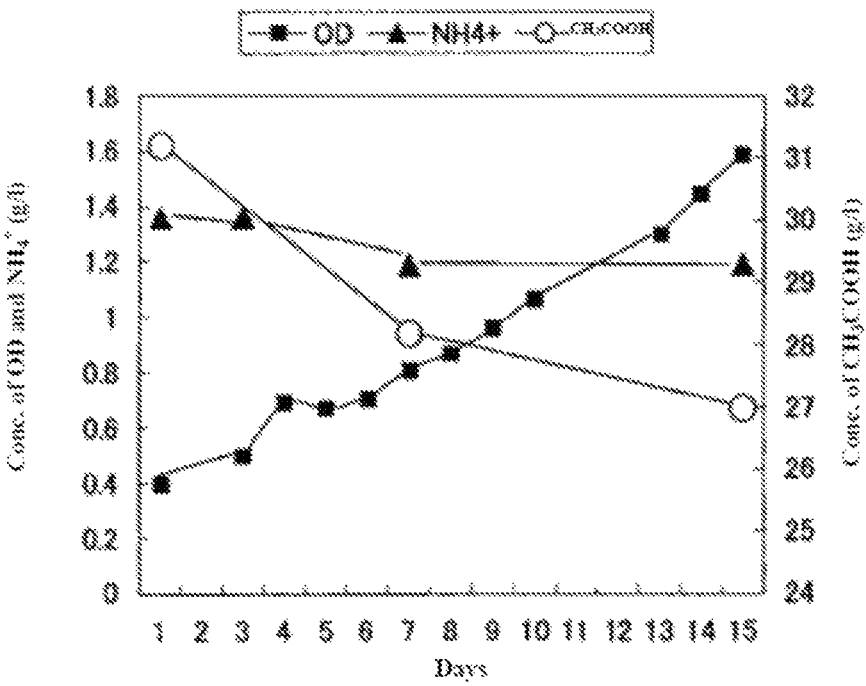
FIG. 2 is a graph showing that the *Alcaligenes faecalis* used in the present invention grew using acetic acid and ammonia under anaerobic conditions.

FIG. 2 shows that the *Alcaligenes faecalis* stated above has grown using (utilizing) acetic acid and ammonia ($NH_4^+$) under anaerobic conditions.

The invention claimed is:

1. A method of inhibiting methanogenesis comprising:
    Applying *Alcaligenes faecalis* to a methane fermentation system, wherein the *Alcaligenese faecalis* uses acetic acid as a substrate under anaerobic conditions.

2. The method of claim 1, wherein the *Alcaligenes faecalis* is *Alcaligenes faecalis* No. 4(FERM BP-11247).

3. The method of claim 1, wherein the methane fermentation system is a ruminant animal.

4. The method of claim 1, wherein the methane fermentation system is paddy field, lake, or aquaculture pond.

5. The method of claim 3, wherein said *Alcaligenes faecalis* is added to a feed for the ruminant animal.

* * * * *